United States Patent
Nam et al.

(10) Patent No.: US 10,806,414 B2
(45) Date of Patent: Oct. 20, 2020

(54) MOBILE X-RAY IMAGING APPARATUS

(71) Applicant: Samsung Electronics Co., Ltd., Suwon-si (KR)

(72) Inventors: Jae-won Nam, Yongin-si (KR); Seung-hwan Lee, Yongin-si (KR); Jung-min Kim, Suwon-si (KR); Ku-il Jang, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 335 days.

(21) Appl. No.: 15/706,557

(22) Filed: Sep. 15, 2017

(65) Prior Publication Data

US 2018/0110490 A1   Apr. 26, 2018

(30) Foreign Application Priority Data

Oct. 20, 2016 (KR) .................. 10-2016-0136247
Jan. 26, 2017 (KR) .................. 10-2017-0012958

(51) Int. Cl.
*A61B 6/00* (2006.01)
*B60B 33/04* (2006.01)

(52) U.S. Cl.
CPC .......... *A61B 6/4405* (2013.01); *A61B 6/4429* (2013.01); *B60B 33/045* (2013.01); *A61B 6/467* (2013.01)

(58) Field of Classification Search
CPC ..... A61B 6/4405; A61B 6/4429; A61B 6/467; B60B 33/045
See application file for complete search history.

(56) References Cited

U.S. PATENT DOCUMENTS

| | | | |
|---|---|---|---|
| 5,503,416 A | 4/1996 | Aoki et al. | |
| 6,539,578 B1* | 4/2003 | Guttmann | B60B 33/0018 16/44 |
| 8,622,614 B2 | 1/2014 | Carmichael et al. | |

(Continued)

FOREIGN PATENT DOCUMENTS

| | | |
|---|---|---|
| CN | 2635403 Y | 8/2004 |
| JP | 06-199101 A | 7/1994 |

(Continued)

OTHER PUBLICATIONS

Extended European Search Report regarding Application No. 17196265.7, dated Mar. 6, 2018, 7 pages.

(Continued)

*Primary Examiner* — Michael C Bryant (57) ABSTRACT

A mobile X-ray imaging apparatus includes a main body performing X-ray imaging by operating an X-ray source, a movable wheel provided in a lower end of the main body and capable of moving the main body, and a support portion comprising a wheel support plate supporting the movable wheel capable of rotating, a frame connected to the main body and supporting the wheel support plate capable of moving, an elastic member disposed between the frame and the wheel support plate and applying an elastic force to the wheel support plate in a direction in which the movable wheel faces a ground, and a stopper restricting a movement of the wheel support plate, wherein the elastic force of the elastic member is smaller than a minimum load applied to the movable wheel.

18 Claims, 8 Drawing Sheets

(56) References Cited

U.S. PATENT DOCUMENTS

| | | |
|---|---|---|
| 9,521,984 B2 | 12/2016 | Moreno Vallejo et al. |
| 2007/0143957 A1 | 6/2007 | Baek |
| 2014/0093051 A1* | 4/2014 | Nishimura ........... A61B 6/4405 378/198 |
| 2014/0265182 A1 | 9/2014 | Stanton et al. |
| 2017/0015140 A1* | 1/2017 | Sekine ................. B60B 33/045 |

FOREIGN PATENT DOCUMENTS

| | | |
|---|---|---|
| JP | 2005-224516 A | 8/2005 |
| KR | 96-0010313 U | 4/1996 |
| KR | 20-1999-0006027 | 2/1999 |
| KR | 20-0412713 Y1 | 3/2006 |
| KR | 10-2016-0030028 A | 3/2016 |

OTHER PUBLICATIONS

Korean Intellectual Property Office Notice of Non-Final Rejection regarding Application No. 10-2017-0012958, dated Mar. 14, 2018, 13 pages.

Notice of Allowance dated Sep. 1, 2018 in connection with Korean Patent Application No. 10-2017-0012958, 7 pages.

\* cited by examiner

MOBILE X-RAY IMAGING APPARATUS

CROSS-REFERENCE TO RELATED APPLICATIONS

This application is related to and claims priority to Korean Patent Application No. 10-2016-0136247, filed on Oct. 20, 2016, and Korean Patent Application No. 10-2017-0012958, filed on Jan. 26, 2017, in the Korean Intellectual Property Office, the contents of which are incorporated herein by reference in their entireties.

TECHNICAL FIELD

One or more embodiments relate to a mobile X-ray imaging apparatus having wheels at a lower end thereof and capable of movement.

BACKGROUND

X-rays are electromagnetic waves generally having a wavelength of about 0.01 to 100 angstroms (Å) and properties of penetrating through an object. X-rays have been widely used with medical equipment for imaging the inside of a live body or non-destructive testing equipment used in general industry.

In an X-ray imaging apparatus using an X-ray, X-rays are output by an X-ray source towards an object and an X-ray detector detects a difference in the strength of X-rays transmitted through the object, thereby obtaining an X-ray image of the object. The X-ray image may be used to identify an internal structure of the object and diagnose the object.

In a general X-ray imaging apparatus, since the X-ray source and the X-ray detector are confined to a specific space, a patient needs to visit a test room where the X-ray imaging apparatus is located and position his/her body with respect to the apparatus for X-ray imaging.

However, since patients having difficulty moving are inconvenienced by X-ray imaging using a general X-ray imaging apparatus, mobile X-ray imaging apparatuses capable of obtaining X-ray images regardless of location have been developed.

A mobile X-ray imaging apparatus having a movable main body is disclosed in which an X-ray source mounted on the main body. Using a portable X-ray detector in combination with the X-ray source, the mobile X-ray imaging apparatus may provide X-ray imaging for patients having difficulty moving.

SUMMARY

To address the above-discussed deficiencies, it is a primary object to provide a mobile X-ray imaging apparatus capable of stable steering during moving under various ground conditions and having improved usability by keeping the apparatus level when using.

Additional aspects will be set forth in part in the description which follows and, in part, will be apparent from the description, or may be learned by practice of the presented embodiments.

According to one or more embodiments, a mobile X-ray imaging apparatus includes a main body performing X-ray imaging by operating an X-ray source, a movable wheel provided in a lower end of the main body and capable of moving the main body, and a support portion comprising a wheel support plate supporting the movable wheel capable of rotating, a frame connected to the main body and supporting the wheel support plate capable of moving, an elastic member disposed between the frame and the wheel support plate and applying an elastic force to the wheel support plate in a direction in which the movable wheel faces a ground, and a stopper restricting a movement of the wheel support plate, wherein the elastic force of the elastic member is smaller than a minimum load applied to the movable wheel.

The mobile X-ray imaging apparatus according to an embodiment may have a constant steering function while moving regardless of a ground condition.

The mobile X-ray imaging apparatus according to an embodiment may be kept level when stopping and performing X-ray imaging, thereby improving usability.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 4D, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Terms such as "part" or "portion" stated in the specification may signify a unit to process at least one function or operation and the unit may be embodied by hardware, software, or a combination of hardware and software. In some embodiments, a plurality of parts or portions may be implemented by one unit or element, or a single part or portion may include a plurality of units or elements. The operating principal and embodiments of the present inventive concept are described below with reference to the accompanying drawings.

Also, in the present specification, an "object", which is subject to imaging, may include a human, an animal, or a part of a human or an animal. For example, an object may include a part of a human body such as body organs or a phantom.

Figure 1:
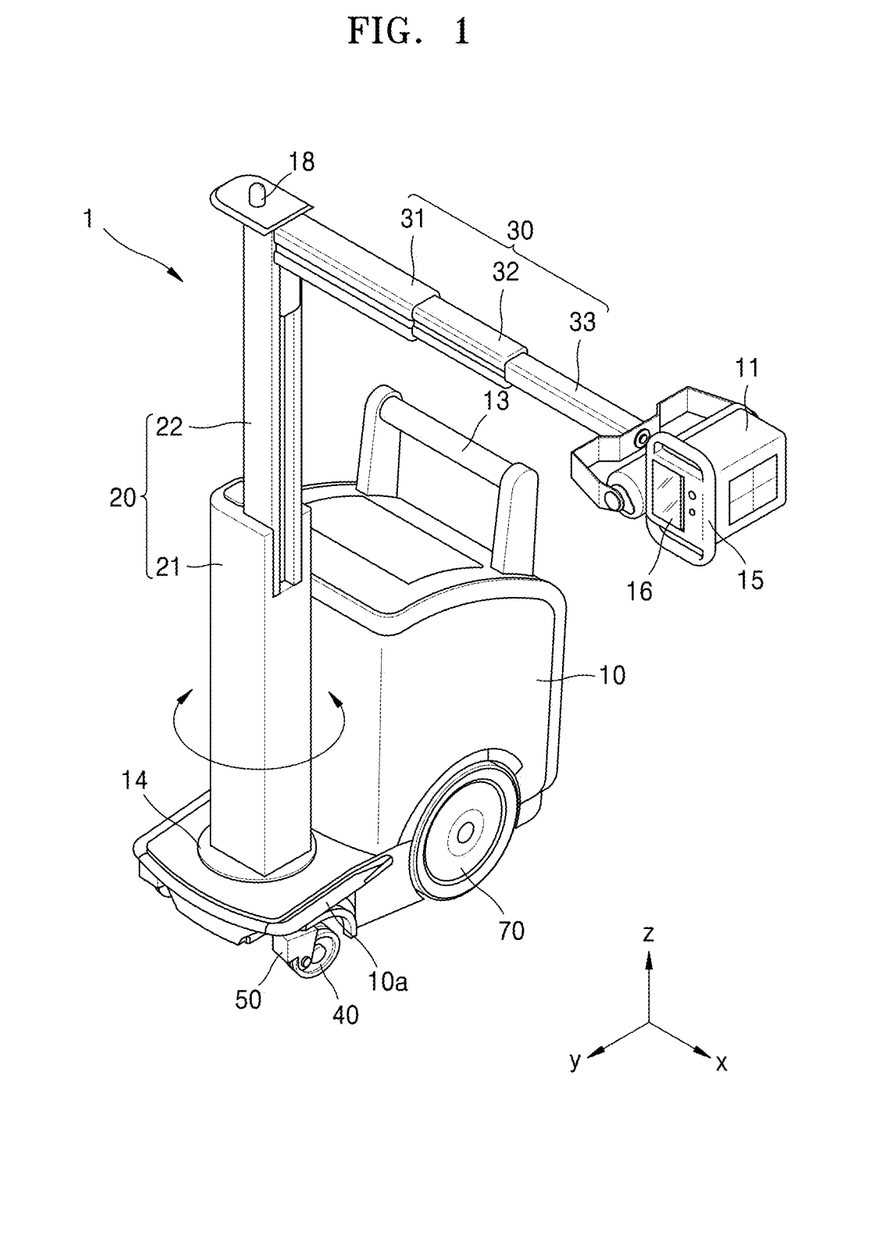
FIG. 1 illustrates a perspective view of a mobile X-ray imaging apparatus according to an embodiment.

FIG. 1 illustrates a perspective view of a mobile X-ray imaging apparatus 1 according to an embodiment.

Referring to FIG. 1, the mobile X-ray imaging apparatus 1 according to the present embodiment may include a main body 10 and an X-ray source 11 mounted on the main body 10.

A movable wheel 40 and a drive wheel 70 may be provided in a lower portion of the main body 10. The main body 10 may include a handle 13, and a user may move the main body 10 by holding and pushing or pulling the handle 13. In FIG. 1, a direction in which the user pushes the handle 13 to move the mobile X-ray imaging apparatus 1 forward is a y direction, and a direction in which the user pulls the handle 13 to move the mobile X-ray imaging apparatus 1 back is a −y direction. The movable wheel 40 may be located in a direction in which the main body 10 moves forward, that is, at a front side, and the drive wheel 70 may be located to the rear of the movable wheel 40. The drive wheel 70 may receive a driving force from a drive source (not shown) such as a drive motor. Alternatively, the mobile X-ray imaging apparatus 1 may be moved only by a user's pushing or pulling force without using the drive source. Although FIG. 1 illustrates the drive wheel 70 to be very larger than the movable wheel 40, the present disclosure is not limited thereto.

The main body 10 may include a control panel 15. The user may control the operation of the mobile X-ray imaging apparatus 1 via the control panel 15. Although FIG. 1 illustrates a configuration in which the control panel 15 is arranged adjacent to the X-ray source 11, the present disclosure is not limited thereto. For example, the control panel 15 may be provided on the main body 10 or may be supported by a control panel support member extending from the main body 10.

The main body 10 may be provided with a column 20 having a pillar shape. The column 20 may include an arm 30 extending in a direction away from the column 20, and the X-ray source 11 may be mounted on the arm 30.

A rotatable panel 14 may be rotatably provided on the main body 10. The column 20 may be mounted on the rotatable panel 14. A front lower end 10a of the main body 10 may protrude and support the rotatable panel 14. The column 20 may rotate with the rotatable panel 14. As the column 20 rotates, the X-ray source 11 connected to the column 20 may rotate and thus a position of the X-ray source 11 may vary. As such, as the X-ray source 11 is provided to have a variable position, X-ray imaging may be performed at various angles.

The column 20 may be capable of vertically extending or retracting. As the column 20 extends or retracts by the user's manipulation, the position of the X-ray source 11 connected to the column 20 may vertically vary. As such, as the X-ray source 11 is provided such that the position of the X-ray source 11 may vertically vary, X-ray imaging may be performed at various heights.

In an example, the column 20 may include a first column 21 and a second column 22 that is extendable from the first column 21. The second column 22 may be the sliding along the first column 21. As the second column 22 slides upward along the first column 21, the length of the column 20 may increase. As the second column 22 slides down along the first column 21, the length of the column 20 may decrease.

The arm 30 may be mounted on the second column 22. The arm 30 may slidably extend from the second column 22. As the arm 30 slides along the second column 22, the vertical position of the X-ray source 11 may vary.

The arm 30 may be extendable, and the X-ray source 11 may be mounted on an end of the arm 30. As the arm 30 extends or retracts by the user's manipulation, the X-ray source 11 may move sideways and thus the position of the X-ray source 11 may vary in a horizontal direction.

In an example, the arm 30 may include a first arm 31 capable of slidabliy extending from the second column 22 and a second arm 32 capable of extending from the first arm 31. Furthermore, the arm 30 may further include a third arm 33 capable of extending from the second arm 32. The X-ray source 11 may be mounted on an end portion of the third arm 33. As the second arm 32 and/or the third arm 33 slides from the first arm 31 in one direction or in the opposite direction, the length of the arm 30 may increase or decrease. The configuration of the arm 30 is not limited to the above description.

The column 20 and/or the arm 30 may include a separate drive source for extending or retracting the column 20 and/or the arm 30, or may be manually extended or retracted without a separate drive source.

To power movement of the mobile X-ray imaging apparatus 1 according to the present embodiment, the main body 10 may have a power source or may be connected to an external power cable to receive power.

Figure 2:
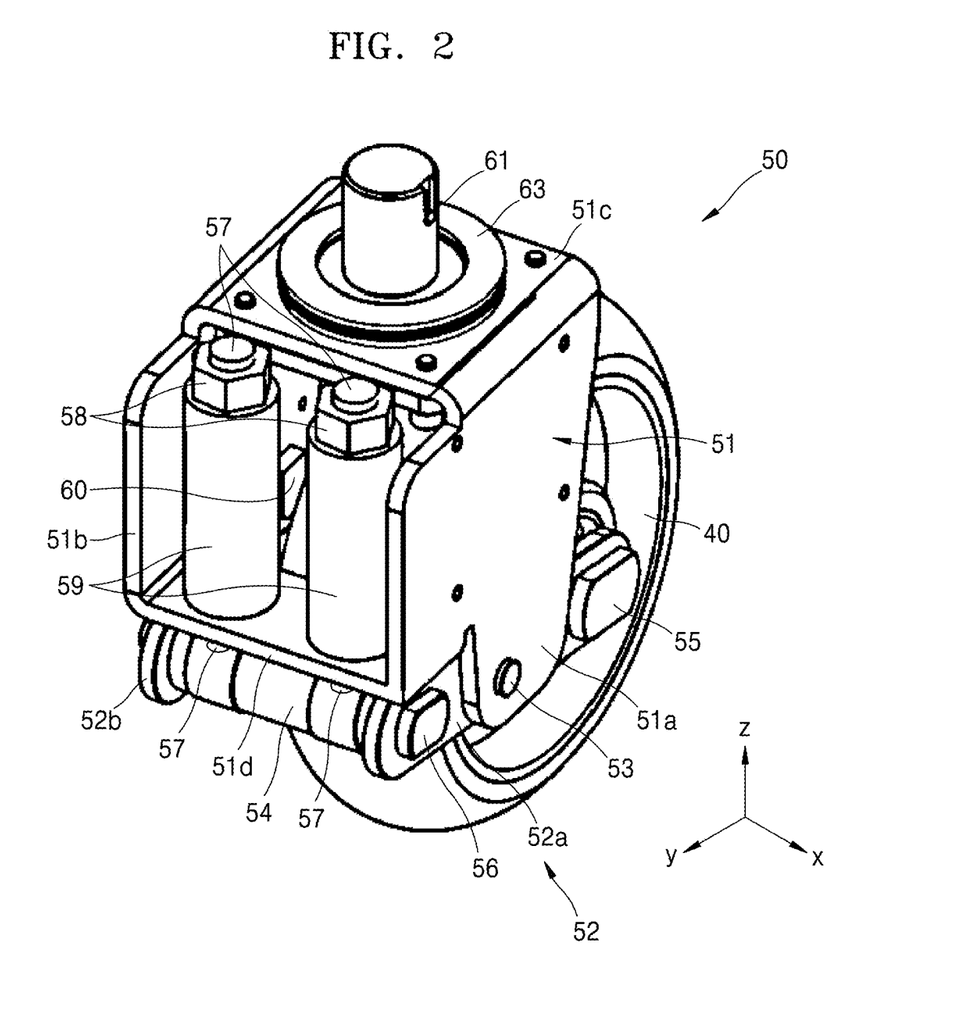
FIG. 2 illustrates an enlarged perspective view of a movable wheel of the mobile X-ray imaging apparatus of FIG. 1 and a support portion supporting the movable wheel.
Figure 3A:
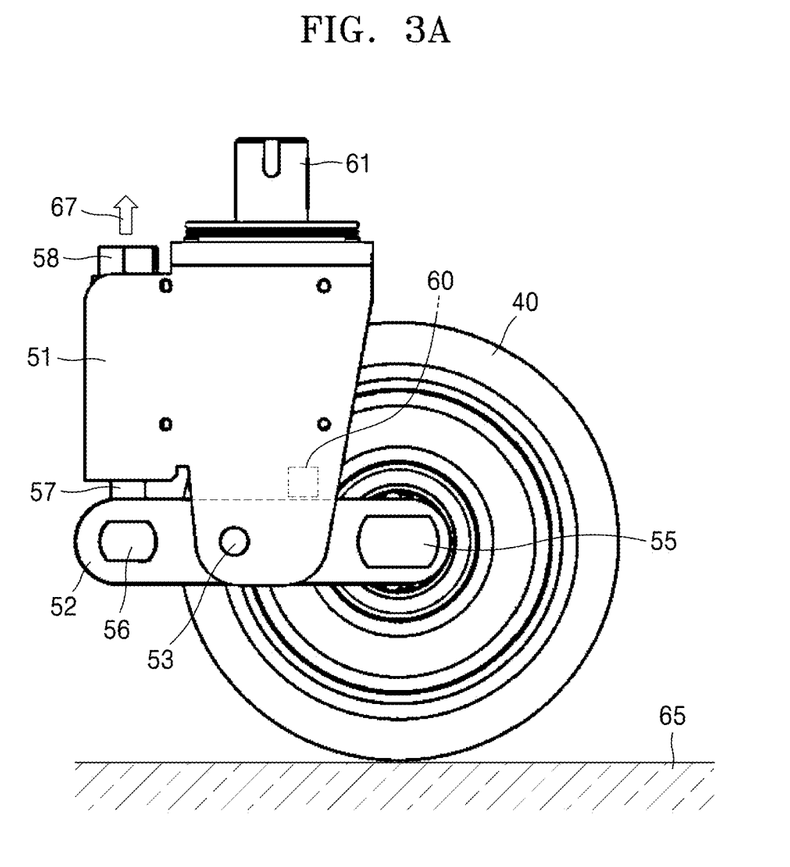
FIGS. 3A and 3B illustrate the position of the movable wheel according to a running state.
Figure 3B:
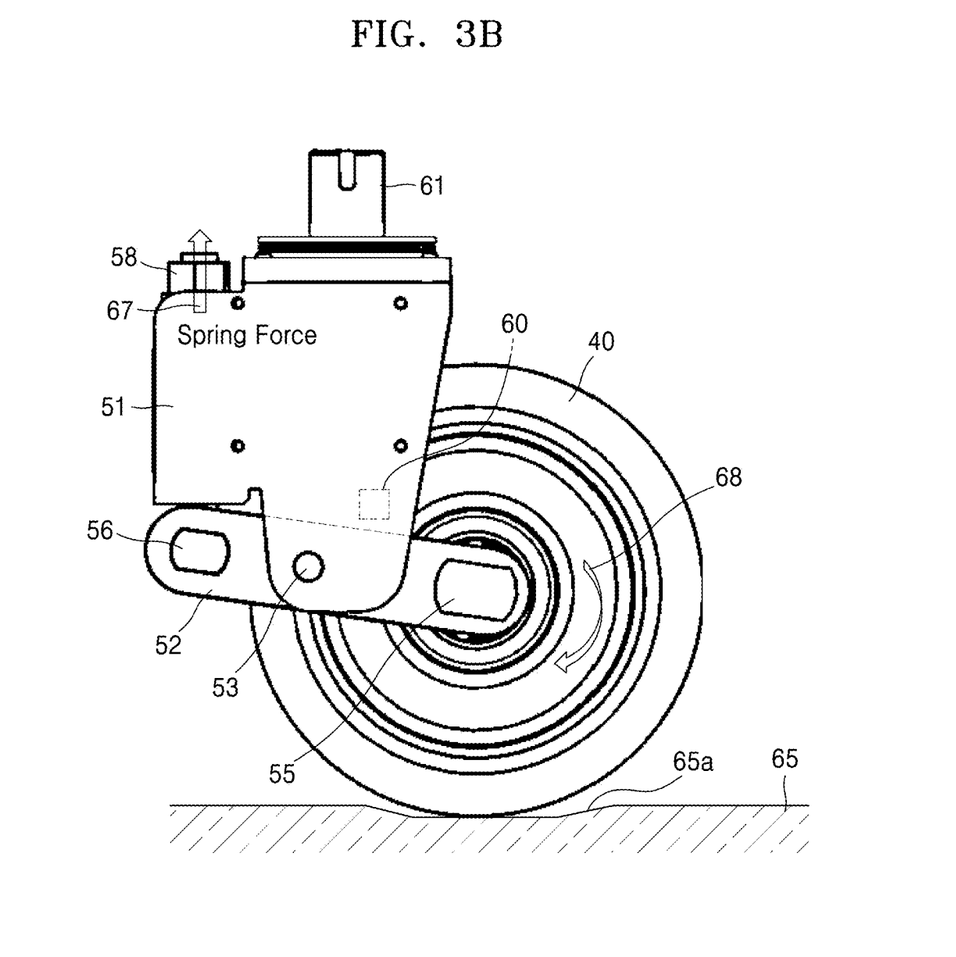

FIG. 2 illustrates an enlarged perspective view of the movable wheel 40 of the mobile X-ray imaging apparatus 1 of FIG. 1 and a support portion 50 supporting the movable wheel 40. FIGS. 3A and 3B illustrate the position of the movable wheel 40 according to a running state.

Referring to FIG. 2, the support portion 50 may include a wheel support plate 52 for supporting the movable wheel 40 capable of rotating, a frame 51 connected to the main body 10 of FIG. 1 and supporting the wheel support plate 52 capable of moving, that is, pivoting, an elastic member 59 provided between the frame 51 and the wheel support plate 52 and applying an elastic force to the wheel support plate 52 in a direction in which the movable wheel 40 faces the ground (−z direction), and a stopper 60 for restricting a movement of the wheel support plate 52.

In an example, the frame 51 may include the first and second frame parts 51a and 51b disposed at both sides of the movable wheel 40, a third frame part 51c connecting upper ends of the first and second frame parts 51a and 51b and coupled to the lower portion of the main body 10, and a fourth frame part 51d connecting one sides of lower ends of the first and second frame parts 51a and 51b. The fourth frame part 51d is at least partially removed to expose the movable wheel 40.

The wheel support plate 52 may include the first and second support plates 52a and 52b arranged on both side surfaces of the movable wheel 40. The first support plate 52a is disposed between the first frame part 51a and the movable wheel 40, and the second support plate 52b is disposed between the second frame part 51b and the movable wheel 40. The first and second support plates 52a and 52b are rotatably coupled by a first rotation shaft 53 to the first and second frame parts 51a and 51b. The movable wheel 40 is rotatably coupled by a second rotation shaft 55 to the first and second support plates 52a and 52b.

A coupling member 54 is disposed between the first and second support plates 52a and 52b and is rotatably coupled by a third rotation shaft 56 to the first and second support plates 52a and 52b. The second rotation shaft 55 and the third rotation shaft 56 are arranged spaced apart from each other with the first rotation shaft 53 interposed therebetween. The coupling member 54 is located under the fourth frame part 51d. The coupling member 54 may be integrally formed with the third rotation shaft 56.

One and of the shaft 57 is coupled to the coupling member 54. Although FIG. 2 illustrates that two shafts are provided as the shaft 57, the present disclosure is not limited thereto and one or a plurality of shafts may be provided as the shaft 57. A hole (not shown) through which the shaft 57 may penetrate is provided in the fourth frame part 51d as many as the number of the shafts 57. The shaft 57 is arranged upward by penetrating through the hole of the fourth frame part 51d. A fixing member 58 such as a nut is provided at the other end of the shaft 57.

The elastic member 59 is arranged between the fourth frame part 51d and the fixing member 58. The elastic member 59, when compressed, exerts an elastic force in a direction to push the fixing member 58 upward with respect to the fourth frame part 51d. The elastic force acting on the fixing member 58 acts in a direction to push the wheel support plate 52 upward with respect to the fourth frame part 51d. As a result, the elastic force acts as a force pressing the movable wheel 40 downward, that is, in a direction toward the ground (−z direction). In other words, the elastic force by the elastic member 59 is transferred to the third rotation shaft 56 of the wheel support plate 52 via the fixing member 58, the shaft 57, and the coupling member 54. In other words, the third rotation shaft 56 of the wheel support plate 52 is a portion that receives the elastic force of the elastic member 59. The third rotation shaft 56 and the second rotation shaft 55 are disposed at the opposite sides with respect to the first rotation shaft 53. Accordingly, due to the elastic force of the elastic member 59, the wheel support plate 52 presses the movable wheel 40 downward, that is, in the direction toward the ground (−z direction) with respect to the first rotation shaft 53.

As described below, as the column 20 and/or the arm 30 extends or retracts, the positions of the X-ray source 11 and the rotatable panel 14 that are heavy are changed with respect to the main body 10. Accordingly, the center of gravity of the mobile X-ray imaging apparatus 1 is changed. As a result, since a load applied to the movable wheel 40 is changed as well, the elastic force of the elastic member 59 is designed to be smaller than the load, that is, the minimum load, applied to the movable wheel 40, with respect to a case when the load applied to the movable wheel 40 is the minimum. Accordingly, even when the elastic force of the elastic member 59 acts as a force pressing the movable wheel 40 downward with respect to the first rotation shaft 53, the movable wheel 40 is moved upward with respect to the first rotation shaft 53 by the load applied to the movable wheel 40.

The stopper 60 is arranged to restrict the upward movement of the movable wheel 40 with respect to the first rotation shaft 53. The stopper 60 may protrude from one or both of inner surfaces of the first and second frame parts 51a and 51b. In an example, the stopper 60 is disposed between the first rotation shaft 53 and the second rotation shaft 55 and above the wheel support plate 52 to restrict the first and second support plates 52a and 52b, that is, a portion close to the second rotation shaft 55 (the portion toward the movable wheel 40), from moving upward over a set value with respect to the first rotation shaft 53. In another example, the stopper 60 is disposed in a lower portion between the first rotation shaft 53 and the third rotation shaft 56 to restrict the first and second support plates 52a and 52b, that is, a portion close to the third rotation shaft 56, from moving downward over a set value with respect to the first rotation shaft 53.

A coupling shaft 61 is arranged between the third frame part 51c and a lower portion of the main body 10. A rotary bearing 63 is provided on the coupling shaft 61 and thus a driving direction of the movable wheel 40 may be changed to the left or right. In this case, the movable wheel 40 functions as a steering wheel.

Next, the operation of the present embodiment the mobile X-ray imaging apparatus 1 is described.

FIG. 3A illustrates that the mobile X-ray imaging apparatus 1 is moving or stands still on a ground surface 65 that is flat. As described above, the elastic force of the elastic member 59 acts as a force pressing the movable wheel 40 downward, that is, in the direction toward the ground. However, since the elastic force of the elastic member 59 is designed to be smaller than the minimum weight applied to the movable wheel 40, the movable wheel 40 is moved upward by the load applied to the movable wheel 40 with respect to the first rotation shaft 53. The stopper 60 is arranged to restrict the upward movement of the movable wheel 40 with respect to the first rotation shaft 53. Accordingly, when the mobile X-ray imaging apparatus 1 is moving or stands still on the ground surface 65 that is flat, the movable wheel 40 contacts the ground surface 65 in a state in which the upward movement of the movable wheel 40 is restricted by the stopper 60. In this case, as described below, even when the column 20 and/or the arm 30 extends or retracts, the height of the movable wheel 40 has no change and the mobile X-ray imaging apparatus 1 may be kept level.

FIG. 3B illustrates that the mobile X-ray imaging apparatus 1 is moving on a partially concave portion 65a in the ground surface 65. Referring to FIG. 3B, in a state in which the elastic force of the elastic member 59 acts as a force pressing the movable wheel 40 downward, that is, in the direction toward the ground, when the mobile X-ray imaging apparatus 1 moving on the ground surface 65 enters the partially concave portion 65a, the movable wheel 40 is separated from the partially concave portion 65a and then pressed against the partially concave portion 65a by the elastic force of the elastic member 59. Accordingly, the movable wheel 40 continues to contact the ground surface 65 while passing over the partially concave portion 65a.

When the movable wheel 40 moves to the left and right functioning as a steering wheel, as the movable wheel 40 is separated from the ground surface 65, a steering function may be lost. However, in the present embodiment, since the movable wheel 40 always contacts the ground surface 65, the steering function may be maintained stable.

FIGS. 4A to 4D illustrate the relationship of a force according to the extension or retraction of the column 20 and/or the arm 30.

Figure 4A:
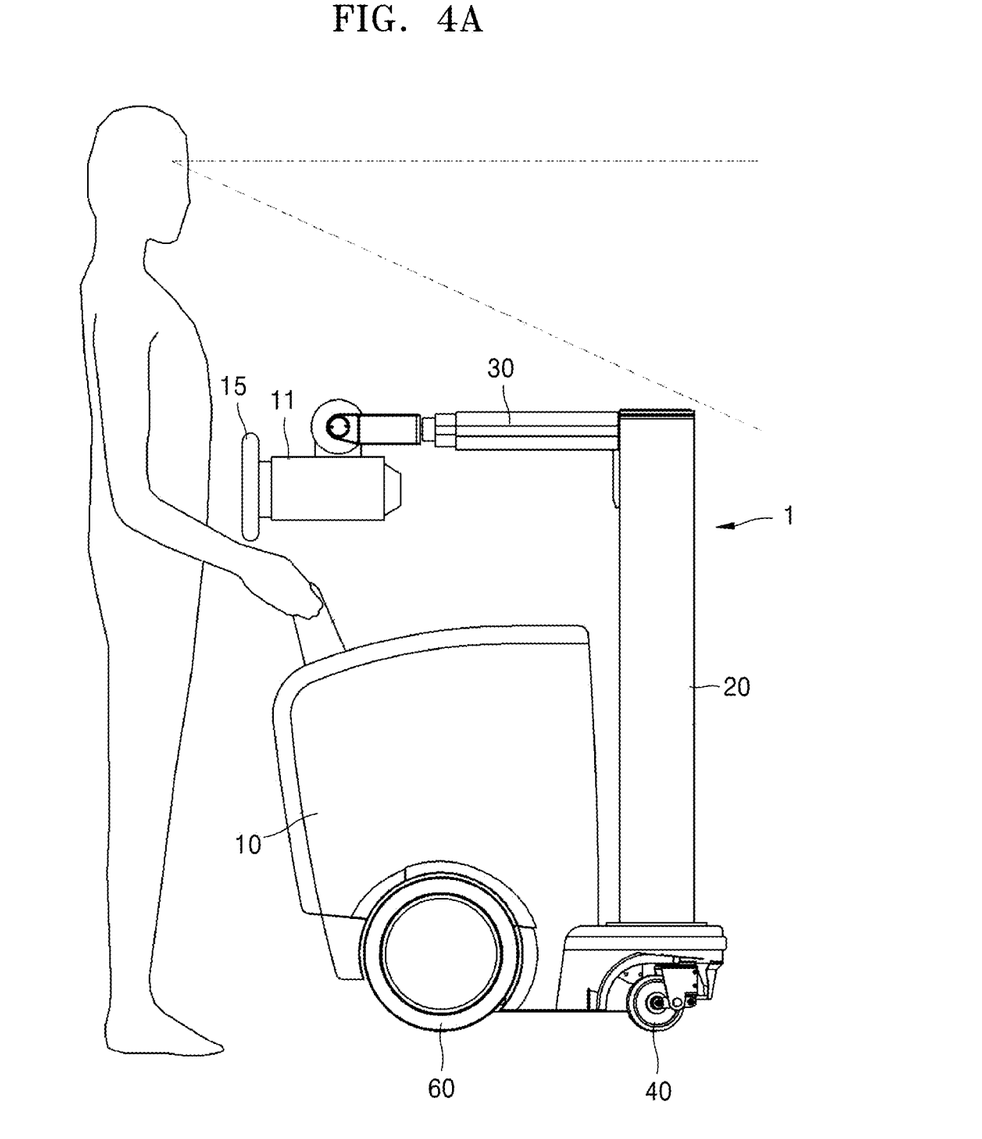
FIGS. 4A to 4D illustrate the relationship of a force according to the extension or retraction of a column and/or an arm.

Referring to FIG. 4A, when the mobile X-ray imaging apparatus 1 is moved by a user, the lengths of the column 20 and the arm 30 may be shortened to secure user's view and prevent collision against an obstacle. The second column 22 may be located overlapping the first column 21 and the second arm 32 is located overlapping the first arm 31, and thus the length of the column 20 and the length of the arm 30 may be reduced. The X-ray source 11 mounted on the arm 30 may be located above the main body 10 to avoid collision against an external obstacle.

In this case, since the X-ray source 11 is relatively close to the column 20, torque applied by the X-ray source 11 to the column 20 and the main body 10 may be relatively small.

Figure 4B:
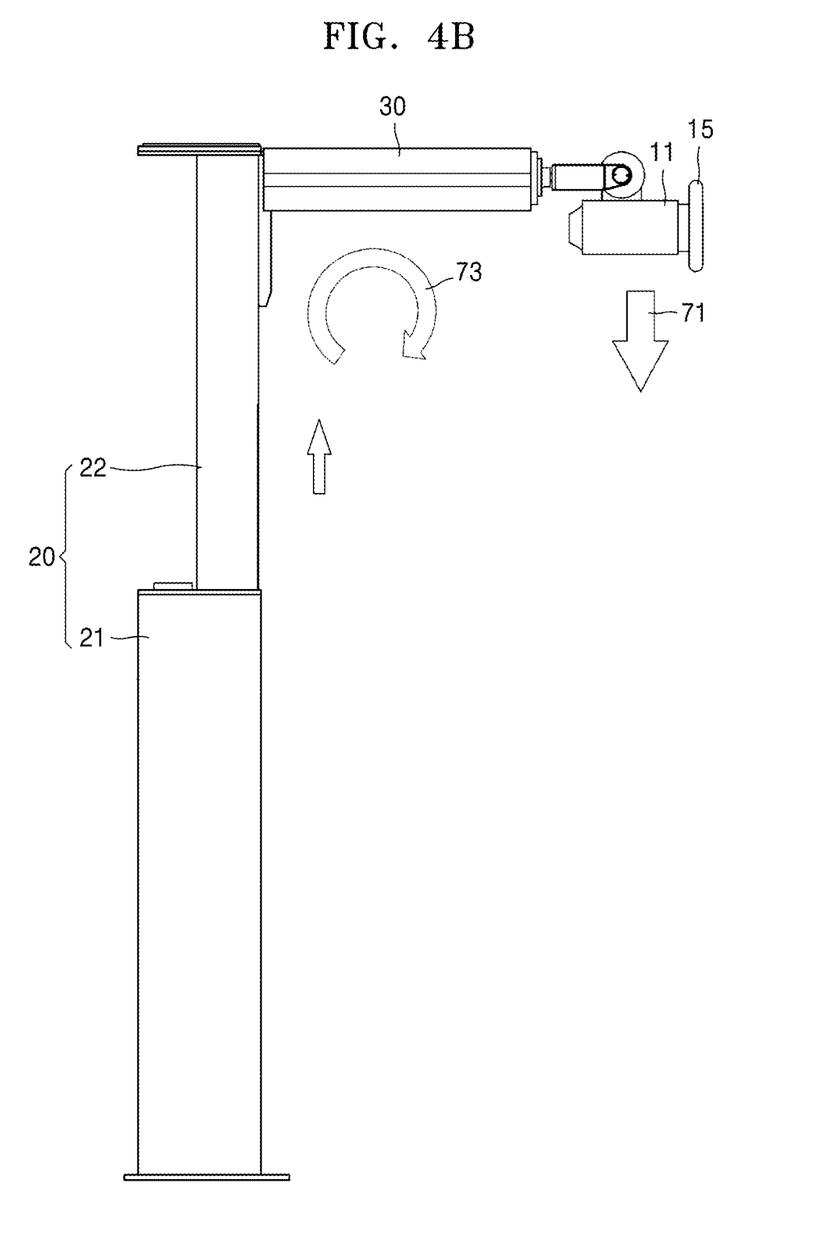

FIG. 4B illustrates that the mobile X-ray imaging apparatus 1 performs X-ray imaging, in which the length of the column 20 extends upward. In this case, due to the weight 71 of the X-ray source 11 and the control panel 15, the main body 10 may receive torque 73 that is greater than the torque in the case illustrated in FIG. 4A. A load applied to the movable wheel 40 may vary according to a change in the torque 73. In the present embodiment, since the height of the movable wheel 40 is always maintained constant, the mobile X-ray imaging apparatus 1 may operates stably.

Figure 4C:
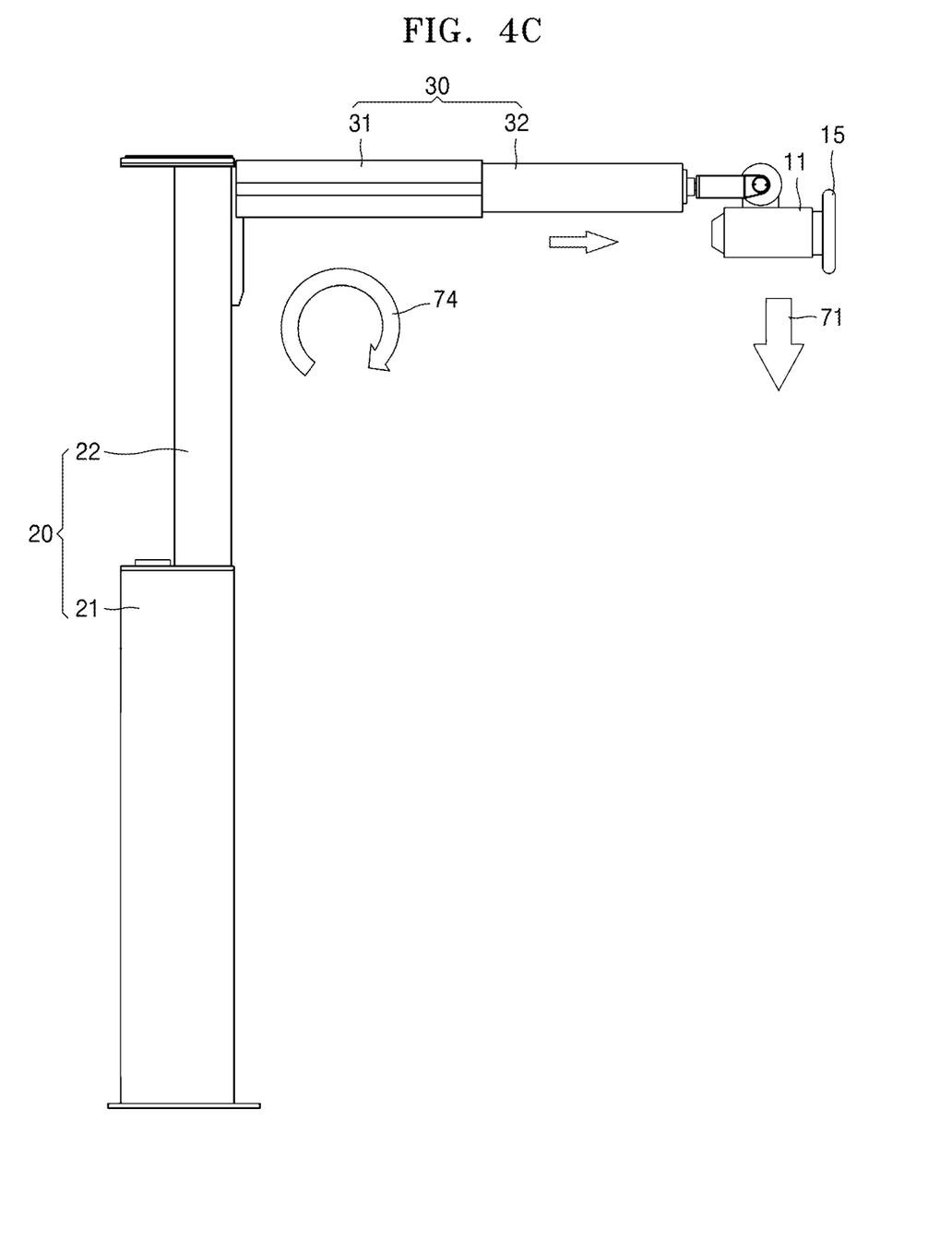
Figure 4D:
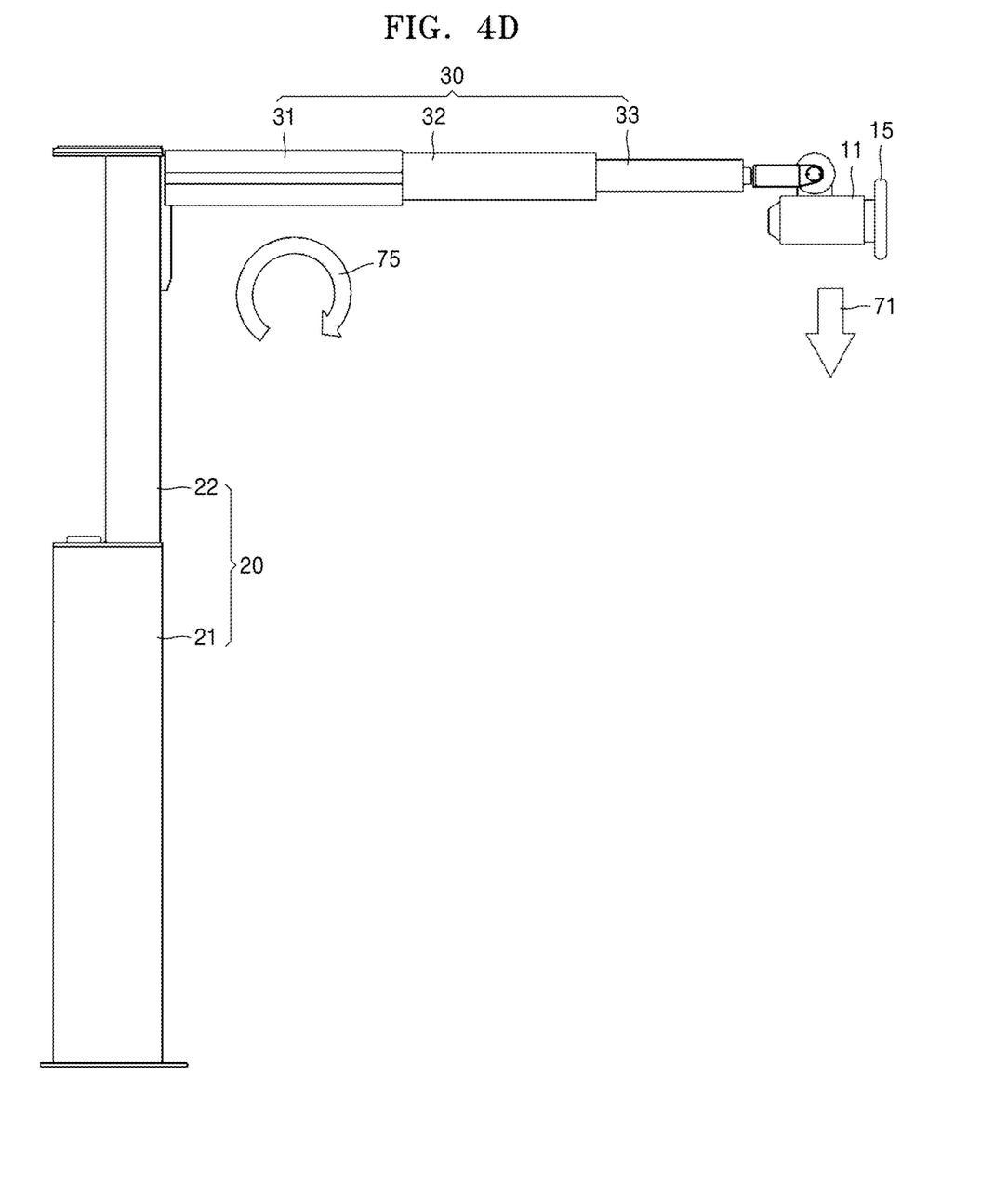

FIGS. 4C and 4D illustrate that the mobile X-ray imaging apparatus 1 performs X-ray imaging, in which the length of the column 20 extends upward and further the arm 30 extends long. As the extended length of the arm 30 increases, torques 74 and 75 due to the weight 71 of the X-ray source 11 and the control panel 15 increase further, and the load applied to the movable wheel 40 may vary according to the movement of the center of weight. As such, as the center of weight of the mobile X-ray imaging apparatus 1 is moved and the torques 74 and 75 due to the weight 71 of the X-ray source 11 and the control panel 15 increase, a risk of the mobile X-ray imaging apparatus 1 falling sideways may increase as well. In a mobile X-ray imaging apparatus according to the related art, it has been tried to obtain driving stability by using elastic suspension by applying an elastic force to a steering wheel, the elastic force being greater than the load applied to the steering wheel. In this case, however, when the load applied to the movable wheel 40 increases, the height of the movable wheel 40 decreases and thus a risk of the mobile X-ray imaging apparatus 1 falling sideways increases further. In contrast, according to the present embodiment, since the height of the movable wheel 40 is always maintained constant, the mobile X-ray imaging apparatus 1 may be stably operated.

It should be understood that embodiments described herein should be considered in a descriptive sense only and not for purposes of limitation. Descriptions of features or aspects within each embodiment should typically be considered as available for other similar features or aspects in other embodiments.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A mobile X-ray imaging apparatus comprising:
   a main body including an X-ray source;
   a movable wheel provided in a lower end of the main body and configured to move the main body; and
   a support portion comprising:
      a wheel support plate supporting the movable wheel, the wheel support plate is configured to rotate,
      a frame connected to the main body and configured to support the wheel support plate, an elastic member configured to apply an elastic force to the wheel support plate in a direction to cause the movable wheel to move downward, and
      a stopper configured to restrict a movement of the wheel support plate, wherein the wheel support plate is configured to rotate around a first rotation shaft and the movable wheel is configured to rotate around a second rotation shaft,
      a first portion of the wheel support plate, to which the elastic force of the elastic member is applied, is located opposite with respect to the first rotation shaft, to a second portion of the wheel support plate, the second portion of the wheel support plate being coupled to the second rotation shaft, and
      the stopper is configured to restrict the movement of the wheel support plate when the main body moves or stands still on a ground surface that is flat.

2. The mobile X-ray imaging apparatus of claim 1, wherein the stopper is disposed between the first rotation shaft and the second rotation shaft and above the wheel support plate.

3. The mobile X-ray imaging apparatus of claim 1, wherein the stopper is configured to protrude from the frame.

4. The mobile X-ray imaging apparatus of claim 1, wherein the movable wheel is a steering wheel configured to change a driving direction of the main body to steer the driving direction of the main body.

5. The mobile X-ray imaging apparatus of claim 1, further comprising a drive wheel that moves the main body by a driving force received from a drive source.

6. The mobile X-ray imaging apparatus of claim 5, wherein the movable wheel is disposed in front of the drive wheel in a driving direction of the main body.

7. The mobile X-ray imaging apparatus of claim 1, further comprising a column extending upward from the main body and an arm extending from the column sideways, wherein the X-ray source is provided on an end portion of the arm.

8. The mobile X-ray imaging apparatus of claim 7, wherein the column is vertically extended or retracted by a user's manipulation.

9. The mobile X-ray imaging apparatus of claim 7, further comprising a rotatable panel rotatably provided on the main body, wherein the column is provided on the rotatable panel.

10. The mobile X-ray imaging apparatus of claim 7, wherein the arm is extended or retracted sideways by a user's manipulation.

11. The mobile X-ray imaging apparatus of claim 7, further comprising a control panel controlling an X-ray imaging operation by a user's manipulation, wherein the control panel is provided on the arm.

12. A mobile apparatus comprising:
   a main body;
   a movable wheel provided in a lower end of the main body and configured to move the main body; and
   a support portion comprising: a wheel support plate supporting the movable wheel, the wheel support plate is configured to rotate;
   a frame connected to the main body and configured to support the wheel support plate;

an elastic member configured to apply an elastic force to the wheel support plate in a direction to cause the movable wheel to move downward; and a stopper configured to restrict a movement of the wheel support plate, wherein the wheel support plate is configured to rotate around a first rotation shaft and the movable wheel is configured to rotate around a second rotation shaft, a first portion of the wheel support plate, to which the elastic force of the elastic member is applied, is located opposite with respect to the first rotation shaft, to a second portion of the wheel support plate, the second portion of the wheel support plate being coupled to the second rotation shaft, and the stopper is configured to restrict a movement of the wheel support plate when the main body moves or stands still on a ground surface that is flat.

13. The mobile apparatus of claim 12, wherein the stopper is disposed between the first rotation shaft and the second rotation shaft and above the wheel support plate.

14. The mobile apparatus of claim 12, wherein the stopper is configured to protrude from the frame.

15. The mobile apparatus of claim 12, wherein the movable wheel is a steering wheel configured to change a driving direction of the main body to steer the driving direction of the main body.

16. The mobile apparatus of claim 12, further comprising a drive wheel that moves the main body by a driving force received from a drive source.

17. The mobile apparatus of claim 16, wherein the movable wheel is disposed in front of the drive wheel in a driving direction of the main body.

18. The mobile apparatus of claim 12, further comprising a column extending upward from the main body and an arm extending from the column sideways.

* * * * *